Figure 1A:
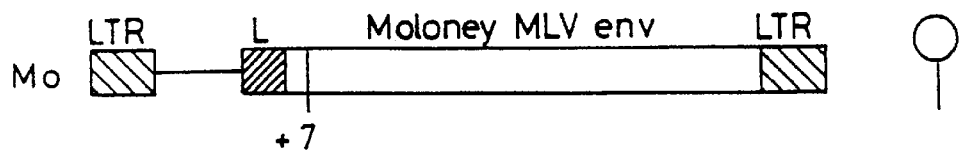
Figure 1B:
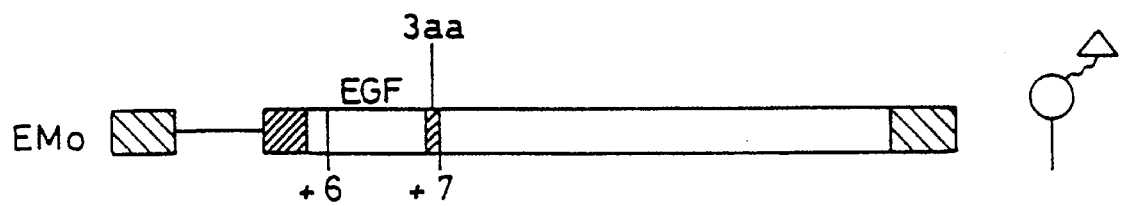
Figure 1C:
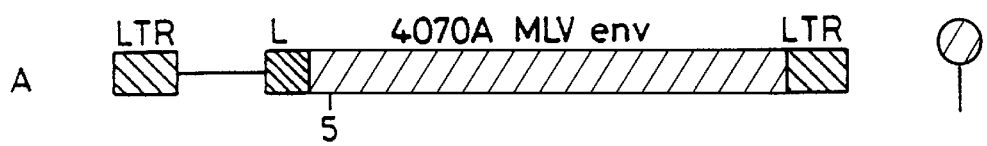
Figure 1D:
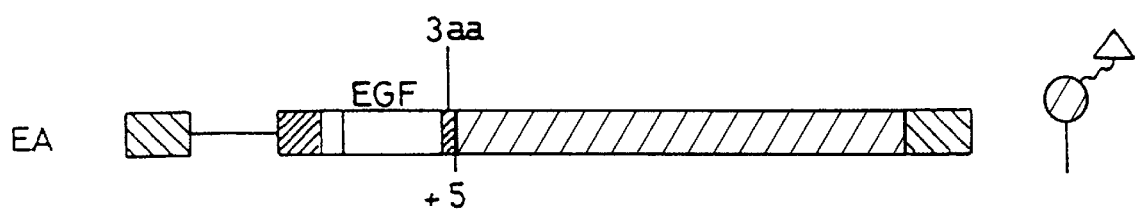

United States Patent [19]
Russell et al.

[11] Patent Number: 6,054,281
[45] Date of Patent: Apr. 25, 2000

[54] BINDING ASSAYS

[75] Inventors: Stephen James Russell; Mark Philip Chadwick; Frances Joanne Bullough, all of Cambridge, United Kingdom

[73] Assignee: Medical Research Council, United Kingdom

[21] Appl. No.: 08/907,392

[22] Filed: Aug. 7, 1997

Related U.S. Application Data

[63] Continuation of application No. PCT/GB96/01693, Jul. 15, 1996.

[30] Foreign Application Priority Data

Jul. 13, 1995 [GB] United Kingdom ................ 9514368

[51] Int. Cl.[7] ............................ G01N 33/53; C12Q 1/00; C12Q 1/70; C12N 7/01
[52] U.S. Cl. ............................ 435/7.1; 435/7.2; 435/7.8; 435/7.93; 435/5; 435/6; 435/235.1; 536/23.6; 536/23.72
[58] Field of Search ............................ 435/7.1, 7.2, 7.8, 435/7.93, 5, 6, 235.1; 536/23.4, 23.72

[56] References Cited

U.S. PATENT DOCUMENTS 5,723,287  3/1998  Russell et al. .............................. 435/5

FOREIGN PATENT DOCUMENTS 9427643  12/1994  WIPO .

OTHER PUBLICATIONS

Cosset, et al, "Retroviral Retargeting By . . . " J. Virol. 69(10): 6314–6322, 1995.
Kasahara, et al, "Tissue–Specific targeting of . . . " Science 266:1373–1376, 1994.
Bevan et al., 1995, Identifying Small–molecule Lead Compounds: The Screening Approach To Drug Discovery, *Trends in Biotechnology 13*, p115–122.
Bosworth & Towers, 1989, Scintillation Proximity Assay, *Nature 341*, p167–168.
Cosset et al., 1995, Retroviral Retargeting by Envelopes Expressing an N–Terminal Binding Domain, *J. Virol. 69*, p6314–6322.
Ecker and Crooke, 1995, Combinatorial Drug Discovery: Which Methods Will Produce the Greatest Value? *Bio/Technology 13*, p351–360.
Hodgson J., 1992, Receptor Screening and the Search for New Pharmaceuticals, *Bio/Technology 10*, p973–980.
Luyten & Leysen, 1993, Receptor Cloning And Heterologous Expression–towards A New Tool For Drug Discovery, *Biotechnology 11*, p247–254.
Matano et al., 1995, Targeted Infection Of A Retrovirus Bearing A Cd4–env Chimera Into Human Cells Expressing Human Immunodeficiency Virus Type 1, *Gen. Virol. 76*, p3165–3169.
Matthews et al., 1994, A Survey Of Furin Substrate Specificity Using Substrate Phage Display, *Protein Science 3*, p1197–1205.
Matthews & Wells, 1993, Substrate Phage: Selection of Protease Substrates by Monovalent Phage Display, *Science 260*, p1113–1117.
Schertler, 1992, Overproduction Of Membrane Proteins, *Curr. Opin. Struct. Biol. 2*, p534–544.
Smith et al., 1995, Rapid Identification of Highly Active and Selective Substrates for Stromelysin and Matrilysin Using Bacteriophage Peptide Display Libraries, *Biological Chemistry 270*, p6440–6449.
Somia et al., 1995, Generation Of Targeted Retroviral Vectors By Using Single–chain Variable Fragment: An Approach To In Vivo Gene Delivery, *Proc. Natl. Acad. Sci. 92*, p7570–7574.
Valsesia–Wittman et al., 1994, Modifications in the Binding Domain of Avian Retrovirus Envelope Protein To Redirect the Host Range of Retroviral Vectors, *J. Virol. 68*, p4609–4619.

*Primary Examiner*—Anthony C. Caputa
*Assistant Examiner*—Brett Nelson
*Attorney, Agent, or Firm*—Banner & Witcoff, Ltd.; Kathleen M. Williams

[57] ABSTRACT

Disclosed is a method of testing a substance for the ability to affect the formation or oligomerization of a complex comprising members of a specific binding pair, a first member of the binding pair being present on the surface of a lipid enveloped particle comprising a transferrable label, said first member of the binding pair being capable of binding to a second member of the specific binding pair present on the surface of a cell, the lipid envelope of the particle being capable of fusing with the membrane of the cell so as to transfer the label to the cell, said transfer being inhibited by formation or oligomerization of a complex between the first and second members of the binding pair, wherein the method comprises reacting the particle and the cell, in the presence of the substance under test, (under conditions which would allow for binding of the first and second members of the specific binding pair in the absence of the substance under test), and detecting the label transferred, if any; together with a composition for use in the assay method of the invention.

22 Claims, 6 Drawing Sheets

BINDING ASSAYS

This application is a continuation of PCT/G896/01693 filed Jul. 15, 1996.

FIELD OF THE INVENTION

This invention relates to a method of performing an assay, and a composition for performing an assay.

BACKGROUND OF THE INVENTION

Cells use their surface receptors to monitor and respond to subtle changes in the composition of their immediate environment. Drugs which block or activate specific receptors can therefore be used to modify cellular functions for medicinal purposes.

During the last two or three decades some of the most profitable drug discoveries have resulted from the detailed analysis of ligand-receptor interactions and the development of simple assays which have been used to screen for compounds that block ligand binding or directly stimulate receptors. Molecular biology has now uncovered a plethora of high molecular weight polypeptide ligands (for examples, see WO 94/27643 [Targeted Genetics Corporation] and references therein) with diverse biological activities and the Human Genome Project promises to uncover many more. Thus, a major challenge for the pharmaceutical industry is to discover new drugs that block or mimic the effects of these ligands, or exhibit greater specificity for receptor subtypes (Luyten & Leysen 1993 Trends in Biotechnology 11, p247).

The process of drug discovery is relatively simple in principle (Hodgson 1992 Bio/Technology 10, p973). Large numbers of compounds are screened using assays that can detect the desired biological activity and "lead" compounds identified in this way are then optimised to meet development criteria (Bevan et al., 1995 Trends in Biotechnology 13, p115; Ecker & Crooke 1995 Bio/Technology 13, p351).

The likelihood of identifying (and successfully optimising) a lead compound would be increased by the use of simple, sensitive assays that can tolerate a high throughput of drug candidates per unit time and by screening as many different compounds as possible.

There are many types of binding assay available, each with its own advantages and disadvantages. Non-equilibrium assays are suitable for detection of high affinity binding reactions whereas equilibrium assays, such as the scintillation proximity assay (Bosworth & Towers, 1989 Nature 341, p167) are required for detection of low affinity binding reactions characterised by rapid dissociation of bound ligand. Assays such as these, that require a pure source of receptor protein, are problematic because it remains difficult to purify membrane receptor proteins in large quantity (Schertler 1992, Curr. Opin. Struct. Biol. 2, p534). Cell-based assays are therefore preferred because most receptors can be expressed easily from cloned DNA.

Usually the ligand is obtained in pure form and labelled, such that it can be easily detected after it has bound to its cognate receptor on the surface of a mammalian cell. Binding to the receptor is monitored by detection of label on the target cells and lead compounds are identified by virtue of their ability to reduce the amount of receptor-bound label. However, it can be problematic to obtain a pure source of the ligand, and attaching a label (e.g. radioiodine, fluorescein, biotin) to the ligand can alter its affinity for the receptor.

Alternatively, the ligand may be attached to a toxic moiety such that binding to the receptor causes the target cells to die; the lead compound is then detected by its ability to prevent the death of the target cells. However, this type of assay is unlikely to detect a typical lead compound with weak blocking activity, insufficient to prevent the delivery of at least some toxin to the target cells.

In other cell-based assays the binding of a ligand to its receptor is detected by measuring a biochemical or physiological response of the target cell. One of the pitfalls of this type of assay is that a compound may block the response of the target cell in other ways than by interfering with ligand binding, giving rise to a large number of false positives.

Ligand-dependent, Receptor-mediated Retroviral Sequestration

Retroviral envelope glycoproteins mediate specific viral attachment to cell surface receptors and subsequently trigger fusion between the viral envelope and the target cell membrane. Retroviral envelope glycoproteins consist of an external glycoprotein moiety (SU) noncovalently attached at its C-terminus to a smaller transmembrane polypeptide moiety (TM). Each surface projection (or spike), visible by electron microscopy on the viral surface, is a trimer of identical envelope glycoprotein subunits. SU comprises two domains connected by a proline-rich hinge, the N-terminal domain conferring receptor specificity and exhibiting a high degree of conservation between murine leukaemia viruses (MLVs) with different host ranges (Battini et al., 1992 J. Virol. 66, p1468–1475).

A general method has been disclosed that allows the display of a polypeptide ligand (which may be glycosylated) on the surface of a retroviral vector as a genetically encoded extension of the viral envelope protein (WO94/06920, Medical Research Council). The engineered retroviral vector then adopts the binding specificity of the displayed ligand. To date several different polypeptide ligands have been displayed on murine leukaemia virus (MLV)-based retroviral vectors, including single chain antibodies, cellular growth factors and immunoglobulin binding domains (WO94/06920 Medical Research Council; Cosset et al., 1994 Gene Therapy 1 pS1; Nilson et al., 1994 Gene Therapy 1, pS17). In principle, this technology should allow the display of many different structural classes of binding domains on retroviral vectors, including glycopolypeptides and glycoproteins.

The present inventors, in collaboration with colleagues, have also recently discovered a novel biological phenomenon called ligand-dependent, receptor-mediated viral sequestration (illustrated in example 1). A polypeptide ligand is fused (by genetic engineering) to the envelope protein of an MLV-based retroviral vector such that the envelope protein to which it has been grafted remains substantially intact and capable of binding to its natural receptor, and the fused non-viral polypeptide ligand is displayed on the viral surface. The virus displaying the fused non-viral polypeptide ligand is then capable of multivalent attachment to the natural virus receptor and to the cognate receptor for the non-viral ligand; attachment to the natural virus receptor leads to infection of the target cell, whereas attachment to the cellular receptor for the displayed non-viral ligand may not lead to infection of the target cell. Where the target cell expresses both species of receptor and attachment through the displayed non-viral ligand does not lead to infection, the two binding reactions (envelope protein to natural receptor and non-viral ligand to its cognate receptor) proceed in competition and the infectivity of the virus for the target cells is reduced in proportion to the efficiency with which the second binding reaction competes virus away from the natural virus receptor.

For example, when epidermal growth factor (EGF) was displayed on an amphotropic retroviral vector, the engineered vector bound preferentially to EGF receptors present on EGF receptor-positive human cells and gene transfer did not occur. EGF receptor-negative cells were fully susceptible to the engineered retroviral vector but showed reduced susceptibility when they were genetically modified to express EGF receptors. The reduction in susceptibility was in proportion to the level of EGF receptor expression. Moreover, when soluble EGF was added to competitively inhibit virus capture by the EGF receptors, gene transfer was restored. The loss of infectivity of the EGF-displaying virus on EGF receptor expressing cells is believed to reflect a block to membrane fusion between the viral envelope and the target cell plasma membrane.

The degree to which gene transfer is inhibited depends, at least in part, on the relative affinities of the two binding reactions (envelope protein to natural receptor and non-viral ligand to its cognate receptor), the relative densities of the two receptors on the target cell surface, and the relative densities of the non-viral ligand and the intact envelope protein on the viral surface. Inhibition of gene transfer is additionally influenced by intrinsic properties of the receptor for the non-viral ligand, such as the distance it projects from the target cell membrane, its mobility within the target cell membrane and its half life on the cell surface after engagement of ligand.

The present invention makes use of these discoveries to provide the basis for a new assay method, ideally suited to the screening of compounds which may affect the binding between a ligand and its receptor.

SUMMARY OF THE INVENTION

In a first aspect the invention provides a method of testing a substance for the ability to affect the formation or oligomerization of a complex comprising members of a specific binding pair ("sbp"), a first member of the binding pair being present on the surface of a lipid enveloped particle comprising a transferrable label, the first member of the binding pair being capable of binding to a second member of the sbp present on the surface of a cell, the lipid envelope of the particle being capable of fusing with the cell so as to transfer the label to the cell, the transfer being inhibited by formation or oligomerization of a complex comprising the first and second members of the binding pair, wherein the method comprises reacting the particle and the cell, in the presence of the substance under test, (under conditions which would allow for binding of the first and second members of the sbp in the absence of the substance under test), and detecting the label transferred, if any.

Detection of the transferred label may be qualitative or, more preferably, quantitative.

By way of explanation, when performing the assay of the invention lipid enveloped particles displaying a first member of a specific binding pair (typically, a cloned ligand molecule) are mixed with cells expressing a second member of the specific binding pair (the respective receptor for the ligand molecule) in the presence of the test compound. Throughout the specification, where the context so permits, "ligand" may generally be taken as being equivalent to "first member" of the sbp and "receptor" may generally be taken as being equivalent to "second member" of the sbp.

Generally speaking, formation of a complex by binding of the ligand to the cell receptor will inhibit fusion of the particle with the cell, thus inhibiting transfer of the label from the particle to the cell. If the substance under test blocks the formation of the complex between the ligand and the receptor, (e.g. by binding to one or both thereof), this will tend to increase the amount of fusion which occurs between the particle and the cell, thereby increasing the amount of label acquired by the cell. Alternatively the test substance may affect the level of expression of the receptor on the surface of the cell (up or down regulation), thus altering the effective concentration of the receptor and thereby altering the likelihood of complex formation between the receptor and the ligand.

Substances which affect either the binding reaction or which affect levels of expression of the receptor are considered as having the ability to affect the formation of a complex between the first and second members of the sbp. Therefore, as used herein, "affect the formation of a complex" refers to interference with the binding reaction between two members of an sbp which bind in the absence of the substance (e.g., a ligand and cognate receptor) or to interference with expression of a receptor and its availability on the cell surface for binding to a ligand.

In addition, the method of the invention may be used to test substances for the ability to affect oligomerization of a complex formed between the first and second members of the sbp, as explained below. As used herein, "affect the oligomerization of a complex" refers to interference with the formation of dimers, trimers, or oligomers, wherein a monomer is a complex comprising first and second binding pairs.

It will be apparent to those skilled in the art that, in particular, the reverse assay method could be used in which binding of the ligand to the cell receptor enhances the amount of fusion, and one would then screen for compounds which can reduce the amount of label acquired by the cell.

It will be noted that, when a particle fuses with a cell, the label may not be, strictly speaking, "transferred" to the cell because the particle may cease to have an independent existence. Thus the label will be acquired by the cell, and such is to be understood as being within the meaning of the term "transferrable label".

It will be appreciated by those skilled in the art that it may not be necessary to add the substance under test at the time the particles are mixed with the cells. It may be sufficient, for example, to pre-incubate the test substance with the particles and/or the cells. If such pre-incubation is used, the particles and/or cells will desirably be washed to remove unbound substance prior to performance of the assay.

Preferably the lipid enveloped particle is a lipid enveloped virus, conveniently a retrovirus. The lipid enveloped particle may however be a synthetic lipid vesicle, liposome or the like.

The second member of the sbp will conveniently be a cell surface receptor, and the first member of the sbp will be a ligand therefor.

The transferrable label may be radioactive, fluorescent or an otherwise-modified lipid or non-lipid component of the lipid enveloped particle. The function of the transferrable label is to indicate mixing of the constituents of the particle with the membrane of the cell. In a preferred embodiment, the transferrable label is a nucleic acid coding for a readily detectable polypeptide (i.e. a reporter gene) which can be expressed in the cell after the particle has fused therewith.

The test substance may be a synthetic compound, or mixture of compounds, or may be a natural product (e.g. plant extract or culture supernatant).

Thus, in preferred embodiments, the invention provides an assay which will indicate not only if a test substance can affect the binding between members of an sbp, but will also indicate if the test substance is toxic to the cell used in the assay. The assay has further advantages in that, typically, the receptor and ligand will be present in their native form (e.g. correctly folded and glycosylated), under physiological conditions (i.e. at body temperature and pH) and (especially in the case of the receptor) expressed on the surface of, for example, mammalian cells. Thus the results of the assay will be more directly relevant to substances of possible medicinal use than those results generated by many existing assay formats.

It is believed that such ligand-customised assays will offer significant advantages over the assays that are currently employed in pharmaceutical drug discovery programmes. They will be simple to perform, easy to read and do not require prior purification of ligand or receptor.

In a particular embodiment, the assay method can be used to screen for substances which affect the level of expression of a receptor on a cell surface.

In a second aspect, the invention provides a composition for use in a binding assay, comprising: a lipid enveloped particle comprising a first member of a specific binding pair and a transferrable label; and a cell displaying a second member of the specific binding pair, the lipid envelope of the particle being capable of fusing with the membrane of the cell so as to transfer the label to the cell, the transfer being inhibited by formation or oligomerization of a complex between the first and second members of the specific binding pair.

The composition may conveniently take the form of a kit, comprising instructions for use according to the method of the invention defined previously.

DRAWINGS

Figure 2:
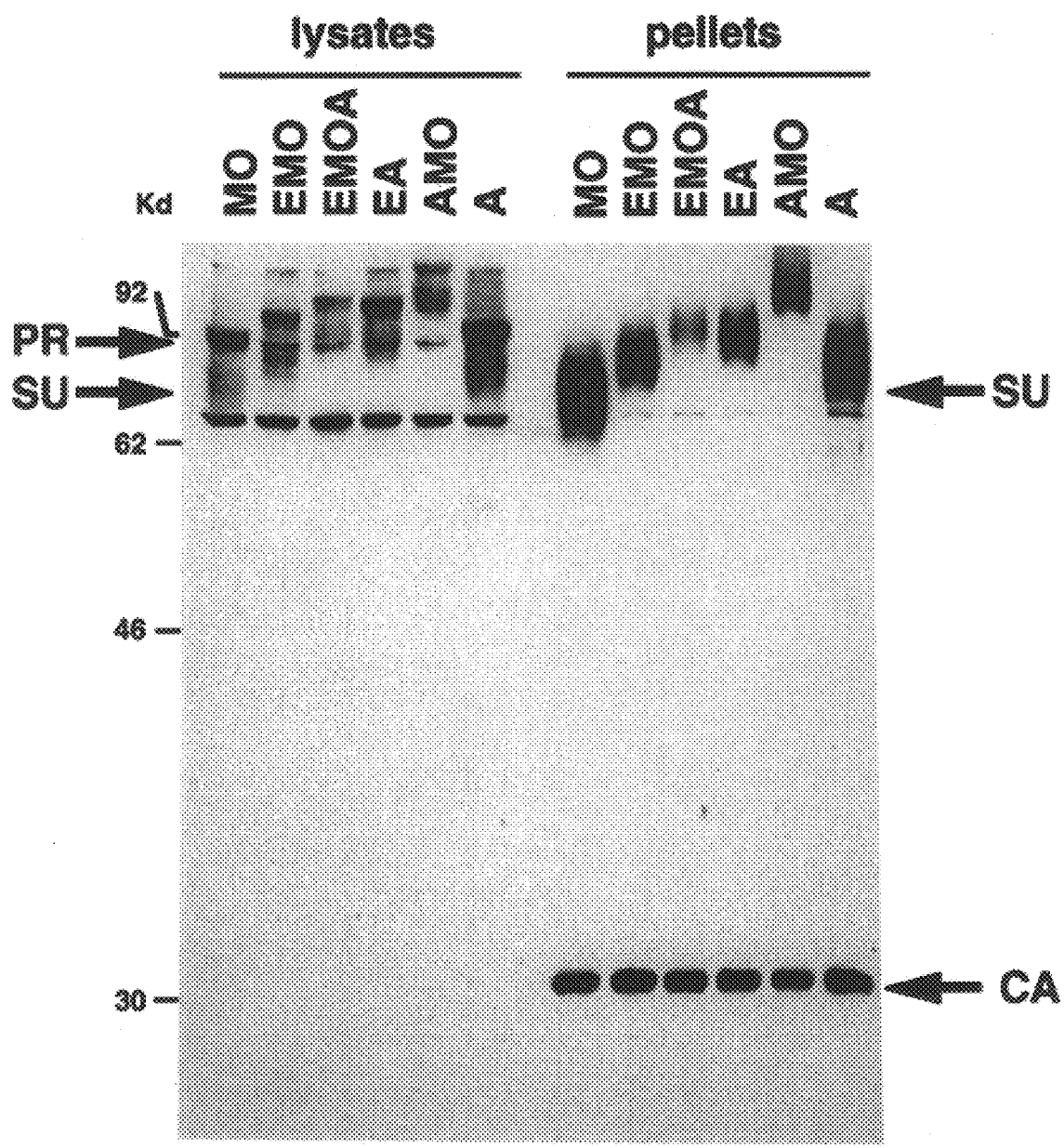
Figures 4A, 4B:
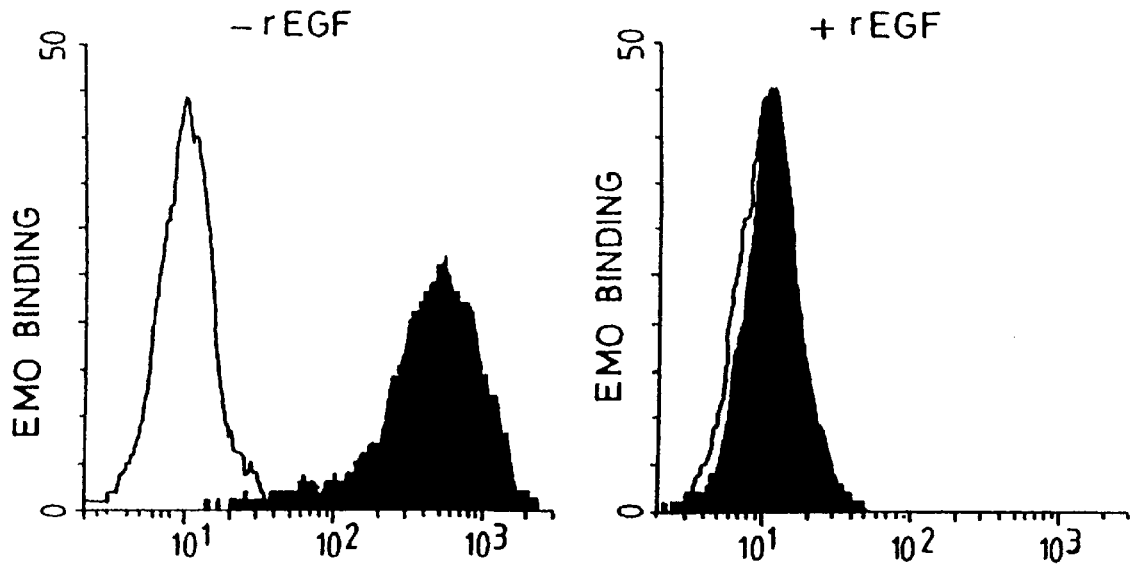
Figures 4C, 4D:
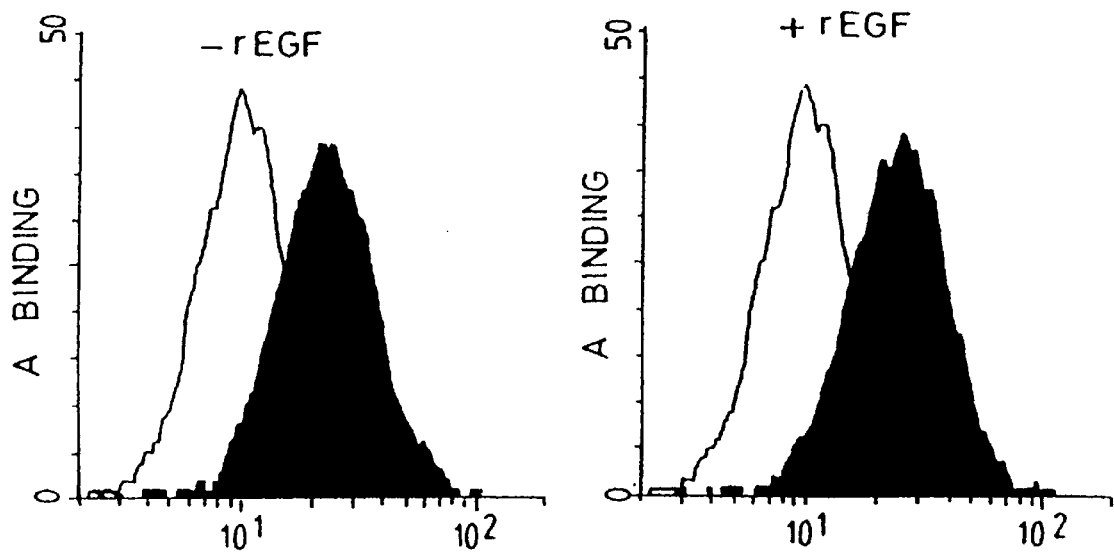
Figure 5:
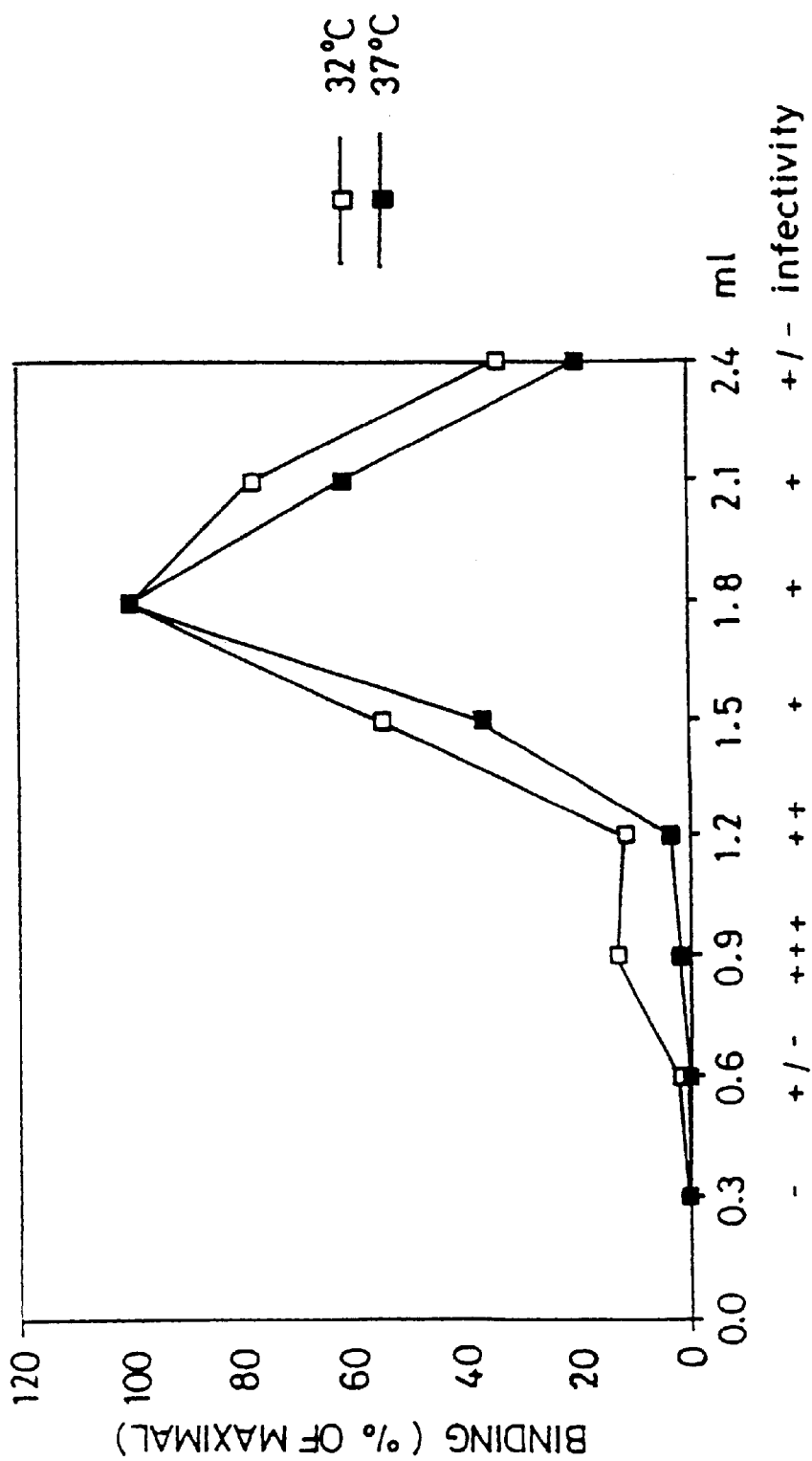

The invention will now be further described by way of illustrative example and with reference to the accompanying drawings, of which:

FIG. 1 is a schematic representation of various wild type and chimaeric retrovirus envelope constructs; (EGF= epidermal growth factor, L=Leader signal sequence from Moloney MLV env; all env genes were expressed using the same promoter, the Friend MLV long terminal repeat "LTR", codon numbering refers to distance from N-terminal of mature SU glycoprotein);

FIG. 2 is a picture of Western blots, showing detection of envelope SU proteins; immunoblots of lysates (on the left) of TELCeB6 cells transfected with the envelopes shown in FIG. 1 or of pellets (on the right) of viral particles produced from these cells. Both blots were stained with an SU anti-serum. The immunoblot of pellets was cut at 46 kD, and the lower part was stained with a p30-CA anti-serum;

FIG. 3 shows a series of graphs produced by fluorescence-activated cell sorting (FACS), illustrating the results of EGF receptor binding assays; cells were A431, HT1080, TE671, or K422. The top row shows binding assays performed using EMO envelopes (black histograms) compared to MO envelopes (white histograms), whilst the bottom row shows the results when the cells were stained with an anti-hEGF receptor (anti-hEGF.R) antibody;

FIG. 4 shows a series of graphs, produced by FACS, illustrating the specificity of EGF binding; A431 cells were used as target cells. Cells were (+rEGF) or were not (-rEGF) treated with recombinant EGF ($10^{-6}$M, 30 min, 37° C.) prior to binding assays using EMO (top row of graphs) or A envelopes (bottom row); and FIG. 5 is a graph showing EGF binding of various fractions (see text) after S-1000 chromatography. Each fraction was analysed both for its binding activity using A431 cells as targets and for infectivity on 3T3 cells: (−): no infectivity, (+/−): 1–10 lacZ-EFU, (+): 10–100 lacZ-EFU, (++): 100–1000 lacZ-EFU, (+++): >1000 lacZ-EFU.

DESCRIPTION

The invention encompasses methods of testing a substance for the ability to affect formation or oligomerization of a complex. The complex includes first and second members of a specific binding pair. The first member of the binding pair is present on the surface of a lipid enveloped particle which includes a transferrable label, where the lipid envelope of the particle is capable of fusing with a cell bearing the second member so as to transfer the label to the cell. Transfer of label to the cell is inhibited by formation or oligomerization of a complex which includes the first and second members of the binding pair.

The method includes the steps of (a) reacting the particle and the cell in the presence of the test substance, under conditions which would permit binding of the first and second members of the binding pair in the absence of the test substance, and (b) detecting the label transferred, if any.

The invention also provides a composition for use in a binding assay, comprising: a lipid enveloped particle comprising a first member of a specific binding pair and a transferrable label; and a cell displaying a second member of the specific binding pair, the lipid envelope of the particle being capable of fusing with the membrane of the cell so as to transfer the label to the cell, the transfer being inhibited by formation or oligomerization of a complex between the first and second members of the specific binding pair.

First Member of Binding Pair and Lipid Enveloped Particles Useful According to the Invention The lipid enveloped particle may be a lipid enveloped virus, conveniently a retrovirus. The lipid enveloped particle may however be a synthetic lipid vesicle, liposome or the like. Fusion between the particle and the cell may be by simple merging of the lipid envelope with the cell, but desirably will be facilitated by inclusion in the particle of one or more polypeptides which are capable of enhancing lipid membrane fusion.

Conveniently the first member of the sbp is a polypeptide which is glycosylated and typically will be of viral origin (i.e. a polypeptide substantially similar to one naturally encoded by a viral gene), conveniently an effective portion of a C type retroviral envelope glycoprotein. Suitable polypeptides are known which can enhance fusion at neutral pH (e.g. retroviral envelope proteins) or at acid pH (e.g. influenza haemagglutinin). It will be appreciated that an effective portion only of such a polypeptide (i.e, a portion sufficient to retain a membrane fusion enhancement function) may be employed, although, for convenience, the polypeptide will preferably be a substantially intact viral envelope protein. The term "substantially intact" in relation to a viral envelope protein is intended to indicate that the protein retains all its domains and is conserved for post-translational processing, oligomerization, viral incorporation and fusogenic activity. However, certain alterations (e.g. substitutions, deletions or additions) can be made to the protein which do not substantially affect these functions. Such polypeptides which enhance fusion frequently require the presence, in the reciprocal membrane, of cognate molecules to allow the fusion enhancing reaction to occur. Such cognate molecules are preferably provided, therefore, on the surface of the cell used in the assay.

Often, when a cell surface receptor binds a ligand, the resulting receptor/ligand complex may undergo oligomerization, which may be essential for signalling to occur. It is suspected that the retroviral envelope trimer must undergo de-oligomerization to expose its fusion domain, and without such de-oligomerization fusion is inhibited. Thus if the ligand displayed on the lipid enveloped particle binds to a receptor to form a receptor/ligand complex, which then undergoes oligomerization, de-oligomerization or exposure of the fusion domain on the retroviral envelope protein will be further inhibited, thereby inhibiting fusion and label transfer.

Thus in particular embodiments the invention may provide an assay for testing a substance for the ability to affect oligomerization of a complex comprising members of an sbp. If a substance inhibits such oligomerization it will tend to promote fusion of the lipid enveloped particle with the cell, so promoting the transfer of label thereto. Such substances may be of considerable interest clinically, as offering means of inhibiting "transforming" signals generated by the products of certain oncogenes, which are mutant receptors or receptor-associated polypeptides.

In a preferred embodiment, the particle comprises a retroviral vector and an effective portion of the 4070A MLV envelope glycoprotein, which molecule enhances fusion between the viral envelope and the cell membrane. Conveniently, the first member of the sbp is displayed as a (genetically encoded) N-terminal extension of the envelope glycoprotein. The term "N-terminal" is intended to apply to fusions at the N-terminal region (i.e. within 30 or so amino acid residues of the N-terminal of the molecule, preferably within 20 or so residues, and more preferably within 10 residues), and not solely to fusions at the extreme N-terminal of the molecule. Use of such a viral vector has the advantage, among others, of allowing for the ready incorporation of different nucleic acid sequences encoding other first members of different sbps.

Second Member of Binding Pair Useful According to the Invention

The second member of the sbp will conveniently be a cell surface receptor, and the first member of the sbp will be a ligand therefor. Examples of suitable sbps are well known (e.g. from WO94/27643). Advantageously the cell will naturally express the surface receptor of interest, but those skilled in the art will appreciate that it is equally possible to transfect the cell with an appropriate expression construct so as to enable the cell to express the receptor of interest. The ligand (i.e. first member of the sbp) may be displayed on the particle as a part of a fusion polypeptide. Such a chimaeric membrane polypeptide may be distinct from the membrane glycoprotein optionally included to facilitate membrane fusion or may form part thereof.

As mentioned above, in addition to the second member of the sbp (i.e. "receptor"), the cell used in the assay may also comprise cognate molecules which interact with fusion-enhancing polypeptides provided on the surface of the particle. The relative densities of these two types of receptor molecule on the surface of the cell can be varied by the use of standard transfection and gene expression methods known to those skilled in the art.

Transferrable Labels Useful According to the Invention

The transferrable label may be radioactive, fluorescent or an otherwise-modified lipid or non-lipid component of the lipid enveloped particle. The function of the transferrable label is to indicate mixing of the constituents of the particle with the membrane of the cell. The label may be a low molecular weight compound, enzyme or other protein whose transfer to the cell is a consequence of fusion between the carrier particle and the cell, and whose presence in (e.g. the cytoplasm or nucleus of) the cell is readily detectable. In a preferred embodiment, the transferrable label is a nucleic acid coding for a readily detectable polypeptide (i.e. a reporter gene) which can be expressed in the cell after the particle has fused therewith. Many reporter genes are known and include chloramphenicol acetyl transferase and β-galactosidase.

Test Substances Useful According to the Invention

The test substance may be a synthetic compound, or mixture of compounds, or may be a natural product (e.g. plant extract or culture supernatant). The duration of contact between the particle and the cell, the temperature and the biochemical composition (e.g. pH, salt concentration, etc.) of the medium in which the contact takes place can be varied and optimised by routine trial-and-error. After sufficient time has elapsed for transfer of the label from the particle to the cell and, where the label is a gene encoding a marker protein, for its expression in the cell, the presence of the label in the cell is detected qualitatively or, preferably, quantitatively. Conveniently, the label is a gene coding for *E. coli* β-galactosidase tagged with a nuclear localisation signal and is readily detected by its ability to cleave X-gal, leading to formation of a coloured product. Gene transfer will be dependent on the presence of an active test compound that blocks the ligand-receptor interaction without damaging the viability of the target cells.

In a particular embodiment, the assay method can be used to screen for substances which affect the level of expression of a receptor on a cell surface. For example, cells expressing a receptor of interest may be incubated under appropriate conditions with a test substance for a period sufficient to allow the test substance to affect the expression level of the receptor molecule. The method of the invention may then be performed and label transferred to the cells detected.

Thus, for example, where the receptor molecule is one to which a ligand displayed on a lipid enveloped particle will bind so as to inhibit transfer of the label to the cell, incubation of the cells with a substance which increases expression of the receptor will have the effect of decreasing the amount of label transferred to the cells by the lipid enveloped particle. Conversely, where the test substance decreases expression of the receptor, the effect will be to increase the amount of label transferred. It has been found that exposure of cells to EGF causes down-regulation of EGF-receptor expression (a negative feedback mechanism) and it is likely that other ligands and mimics thereof will have similar effects on the expression of their cognate receptor.

Generally the cell used in the method of the invention will advantageously be eukaryotic (e.g. a yeast or insect cell) but could be bacterial. The cell will preferably be living (at least at the start of the assay) but could be dead, or even a synthetic inert cell equivalent (such as a synthetic lipid vesicle, liposome or planar lipid membrane). Most desirably the cell will be mammalian, conveniently a cell line.

EXAMPLES

In an attempt to target retroviral gene delivery through the human epidermal growth factor receptor (EGFR) to EGFR-positive cells, the inventors and their colleagues constructed a chimaeric envelope construct in which the human EGF coding sequences were cloned, in frame, into a SfiI-NotI cloning site which had been introduced between the 6th and 7th codons of the env gene of Moloney MLV (Russell et al, 1993 Nucleic Acids Research 21, 1081–1085; Russell et al, WO94/06920). This chimaeric envelope construct (EMO) was then transfected into the complementing cell line TEL-CeB6 which expresses MLV gag and pol functions and a packagable RNA transcript coding for β-galactosidase. The transfected TELCeB6 cells released retroviral particles which efficiently incorporated the chimaeric EMO envelope glycoprotein, as shown by western blot analysis of pelleted virus. Viruses incorporating the chimaeric EMO envelope glycoprotein were shown by chromogenic substrate assay to transfer the β-galactosidase gene to mouse NIH3T3 cells, indicating that the chimaeric protein could still bind to the ecotropic MLV receptor and catalyse membrane fusion.

Viruses incorporating the chimaeric EMO envelope glycoprotein were then separated from soluble (shed) envelope glycoprotein by sephacryl column chromatography of 0.45 μM-filtered culture supernatant and were shown by immunofluorescence staining to bind efficiently to EGF.R-positive human cell lines (i.e. cell lines expressing EGF receptor). Binding to these cells was competitively inhibited by soluble EGF. However, the bound virus did not transfer a functional β-galactosidase gene to the human cell lines, whereas control viruses incorporating the amphotropic 4070A envelope efficiently transferred the β-galactosidase gene to these same human cell lines.

The inventors and colleagues next examined the efficiency of gene transfer to EGFR-positive human cells using recombinant retroviruses displaying the EGF polypeptide fused to the amphotropic 4070A envelope glycoprotein. The chimaeric EGF-4070A (EA) expression construct was created by substituting most of the MoMLV env sequence in FBEGFMosA (from codon 7, immediately 3' of the NotI cloning site to the ClaI site close to the 3' end of the env gene) for corresponding 4070A env sequence (from codon 5 to the ClaI site close to the 3' end of the env gene).

Recombinant retroviruses displaying the chimaeric EA envelope protein behaved in an unexpected fashion. They transferred the β-galactosidase gene efficiently to mouse NIH3T3 cells and to human cells that were negative for EGF receptor expression, but not to EGF receptor-expressing human cells. The titre reduction on EGF receptor-positive human cells was as much as ten million-fold compared to control viruses incorporating unmodified 4070A amphotropic envelopes.

Subsequent experiments using various target cells of mouse and human origin, some of which had been transfected with an EGFR expression plasmid, proved that viruses displaying the chimaeric EMO and EA envelope glycoproteins had selectively impaired ability to infect ecotropic or amphotropic MLV receptor-positive cells that also expressed EGF receptors. Higher levels of EGF receptor expression were associated with greater impairment of infectivity. Cells transfected with an EGF receptor expression plasmid became selectively resistant to EMO and EA viruses, and this resistance was reversible upon treating the cells with soluble EGF to block/downregulate the EGF receptors. Thus, retroviral host range was selectively restricted to EGF receptor-negative cells by displaying a high affinity ligand for EGF receptors on the viral surface.

The present inventors and their colleagues thus discovered a novel biological phenomenon which they have called ligand-dependent, receptor-mediated viral sequestration—a method by which to restrict the host range of a MLV or MLV-based retroviral vector in a ligand-dependent fashion. The first step is to identify a polypeptide ligand which binds specifically to a cell surface marker present on nontarget cells but absent from the target cell population. This polypeptide is then fused (by genetic engineering) to the retroviral envelope protein such that the envelope protein to which it has been grafted remains substantially intact and capable of binding to its natural receptor, and the fused non-viral polypeptide ligand is displayed on the viral surface. The virus displaying the fused non-viral polypeptide ligand is then capable of multivalent attachment to the natural virus receptor and to the the cognate receptor for the non-viral ligand; attachment to the natural virus receptor leads to infection of the target cell, whereas attachment to the cellular receptor for the displayed non-viral ligand may not lead to infection of the target cell. Where the target cell expresses both species of receptor and attachment through the displayed non-viral ligand does not lead to infection, the two binding reactions (envelope protein to natural receptor and nonviral ligand to its cognate receptor) proceed in competition and the infectivity of the virus for the target cells is reduced in proportion to the efficiency with which the second binding reaction competes virus away from the natural virus receptor.

The degree to which gene transfer is inhibited will therefore be influenced by the relative affinities of the two binding reactions, the relative densities of the two receptors on the target cell surface, and the relative densities of the non-viral ligand and the intact envelope protein on the viral surface. Inhibition of gene transfer is additionally influenced by intrinsic properties of the receptor for the non-viral ligand, such as the distance it projects from the target cell membrane, its tendency to oligomerise upon binding ligand, its mobility within the target cell membrane and its half life on the cell surface after engagement of ligand. This method of host range restriction may be applicable to the membrane spike glycoproteins of other enveloped viruses, and to the attachment proteins of non-enveloped viruses such as the adenovirus fibre protein. Where an enveloped virus has multiple distinct membrane spike glycoproteins with differing binding specificities and fusogenic capabilities (eg Paramyxoviridae, Herpesviridae), the restriction of virus host range by this method may or may not require the modification of more than one of the glycoproteins.

The discovery offers a novel strategy for targeting retroviral gene delivery by host range extension (which is the subject of International Patent Application WO 96/00294). After binding to its receptor, EGF is endocytosed and routed to lysosomes, where EGF-EGF receptor complexes are degraded (Carpenter & Cohen, 1990 J. Biol. Chem. 265 p7709–7712). The inventors suspected that viruses bound to EGF receptors might therefore also be rapidly endocytosed and routed to lysosomes for degradation. The inventors therefore attempted to rescue EMO-carrying viral particles from this degradative pathway by treating infected human cells with chloroquine phosphate, a lysosomotropic base which inhibits lysosomal acidification. Viruses carrying unmodified Moloney envelopes (which do not bind efficiently to human cells) were unable to infect the human cell lines, irrespective of the presence of chloroquine. In contrast, viruses carrying EMO envelopes which were shown to bind efficiently to EGF receptors on human cells showed significant infectivity on human EGF receptor-positive cells in the presence of chloroquine. In contrast, there was no evidence of infection in the presence of chloroquine on EGF receptor negative K422 B cells, to which the EMO virus did not bind.

The present inventors realised that this discovery was not only of importance in the field of gene therapy, but could provide the basis for a method of screening substances for their ability to affect the binding between members of a specific binding pair, as set out previously.

Example 1
Construction of Chimaeric Retroviral Envelopes

The sequence coding for EGF (epidermal growth factor) was inserted in MLV (murine leukemia virus) env gene in a position corresponding to amino-acid +6 in the SU glycoprotein of MoMLV (FIG. 1). This position of insertion was previously shown to allow the functional display of single chain antibodies at the surface of virions (Russell et al, 1993 NAR 21 p1081–1085). The EGF domain was separated from the wild type receptor binding domain in the envelope by a small linker containing 3 alanine residues. In the chimera EMO, EGF was inserted in the Mo-MLV envelope, whereas chimera EA had an EGF insertion in the MLV amphotropic (4070A) envelope at position +5. Envelopes, including the control envelopes from ecotropic (MO) and amphotropic (A) MLV, were transfected into TELCeB6 cells which express MLV gag-pol core particles and a lacZ retroviral vector.

Expression and Viral Incorporation of Chimaeric Envelopes

Lysates of TELCeB6 cells were analysed for envelope expression using antibodies against MLV SU (FIG. 2). For both chimeric envelopes, both a precursor and a processed SU product were detected at ratios similar to wild-type envelopes, suggesting that the mutants were correctly expressed and processed. Cell surface expression of mutant envelopes was examined by FACS analysis of producer cells, using antibodies against the SU or a monoclonal anti-hEGF antibody. All transfected cells were stained with the anti-SU antibodies, and cells expressing the EGF-fusion envelopes were also stained with anti-EGF monoclonals (data not shown).

To demonstrate incorporation of the chimeric envelope glycoproteins into retroviral particles, supernatants of the various TELCeB6-transfected cell lines were ultracentrifuged to pellet viral particles. Pellets were then analysed on immunoblots for their content of gag (p30-CA) and envelope proteins (FIG. 2). The chimaeric SU glycoproteins were detected at a similar ratio to gag compared to wild-type envelope.

Binding of Chimaeric Envelopes to EGF Receptors

Human cell lines expressing different numbers of EGF receptors (FIG. 3 bottom) were used for binding assays. Cells were incubated with virus supernatants and binding of viral envelopes to the target cell surface was analysed by FACS using antibodies against the MLV SU.

MoMLV-derived EGF-fusion envelopes (EMO envelopes) were found to bind to A431 cells (FIG. 3 top) over-expressing EGF.R (FIG. 3 bottom). Less binding was found on TE671 and HT1080 target cells which express less EGF.R (FIG. 3). No binding could be detected on K422 lymphoma cells with no detectable expression of EGF receptor (FIG. 3). The EA envelopes bound to A431 cells as well as EMO (data not shown). EGF receptors on A431 cells were down-regulated by pre-incubation with EGF. This treatment did not affect the binding of amphotropic envelopes (FIG. 4 bottom) but abolished binding of EMO envelopes (FIG. 4 top).

SU envelope glycoproteins of MLVs are known to be weakly associated with their TM protein counterparts (Gliniak et al, 1991 J. Biol. Chem. 266 p22991–22997) and a very low proportion of SU is retained on virions. Therefore it is likely that binding assays in FIG. 3 are due in part to soluble envelope glycoproteins shed from virions. To determine whether viral particles could also bind, the supernatant of producer cells was separated by gel-filtration and fractions were analysed for binding activity on A431 cells (FIG. 5). As expected, very little binding activity was found in the early fractions containing the viral particles, with most of the binding activity in the late fractions containing soluble envelopes. However when viral particles were produced at 32° C. in order to reduce the dissociation between SU and TM a significant binding activity was also found in the fractions containing the virions (FIG. 5), demonstrating that viral particles could bind EGF.R.

Host Range Properties of Viruses Carrying EMO Envelopes

Table 1A shows that viruses incorporating EMO envelopes can infect NIH3T3 mouse fibroblasts. Infection is through the ecotropic MLV receptor because the EMO virus cannot infect NIH3T3 cells expressing the Moloney envelope glycoprotein but can infect those expressing the 4070A envelope glycoprotein. Viruses incorporating EMO envelopes can not only bind to EGF receptors but can also bind and infect cells through ecotropic MLV receptors.

Figure 3A:
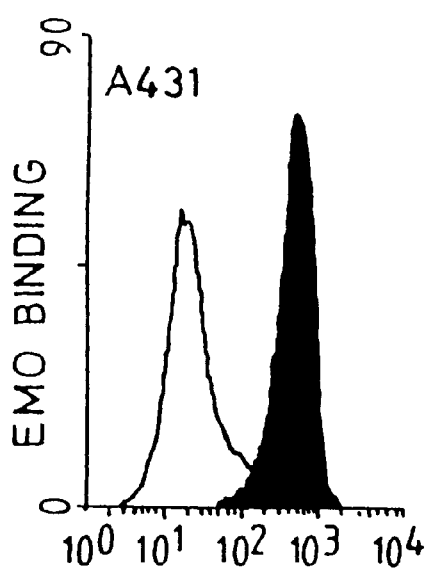
Figure 3B:
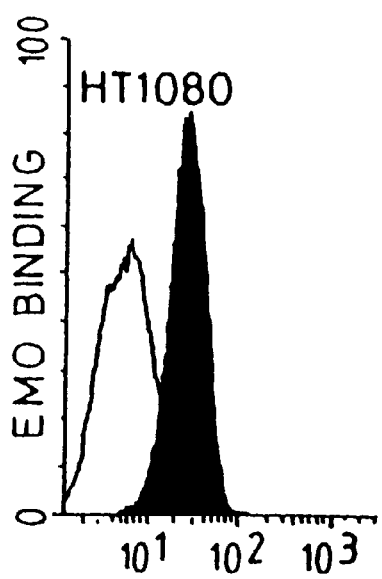
Figure 3C:
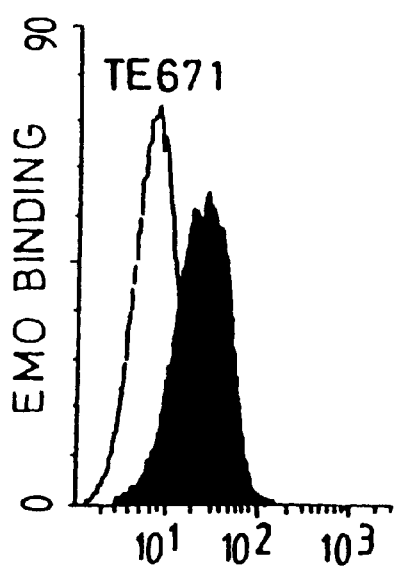
Figure 3D:
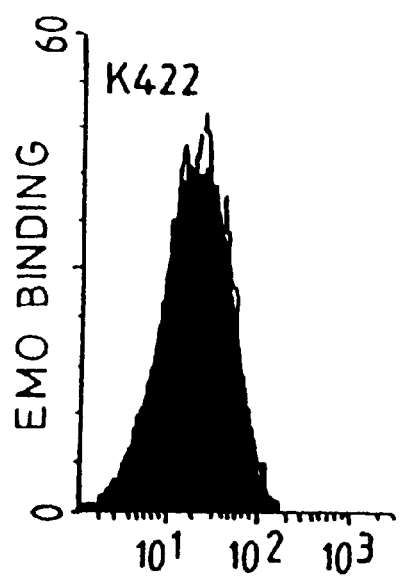
Figure 3E:
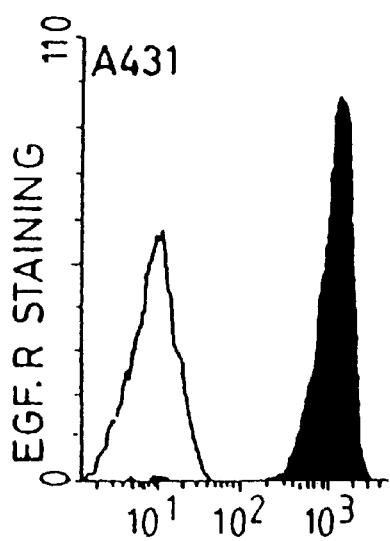
Figure 3F:
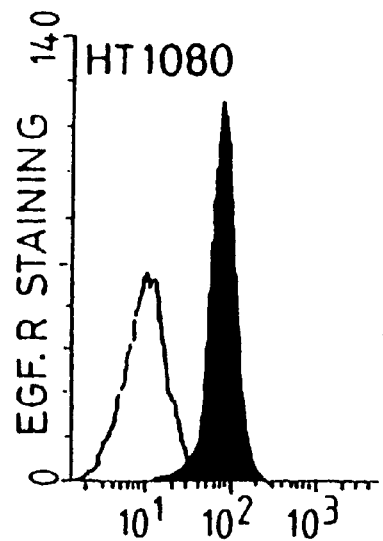
Figure 3G:
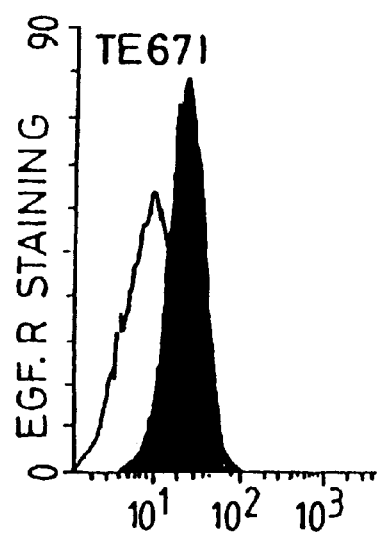
Figure 3H:
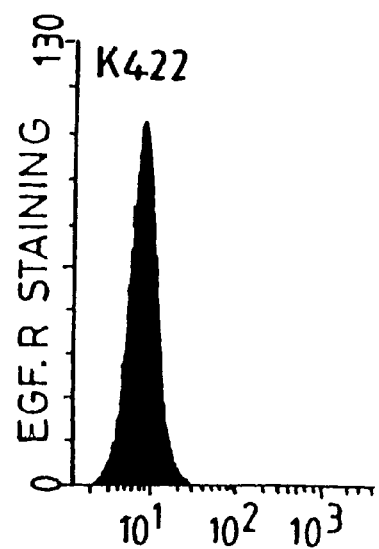

Table 1B shows that viruses incorporating EMO envelopes could not infect human cells expressing various densities of EGF receptors, despite their ability to bind to the EGF receptors on these cells (FIG. 3A). Surprisingly, the cell line EJ.A1, which stably expresses ecotropic MLV receptors from a transfected plasmid, could not be infected by the EMO virus, but was readily infected by viruses incorporating unmodified MO envelopes. This result suggested that the EMO virus could be competitively sequestered by EGF receptors on EJ.A1 cells, preventing it from binding to the ecotropic viral receptors.

Competitive Sequestration of Viruses Carrying EMO Envelopes

To test the idea that EMO viruses could be competitively sequestered by EGF receptors at the surface of an otherwise permissive target cell, the inventors titrated viruses incorporating EMO or MO envelopes on mouse fibroblasts (NR6 and NIH3T3) expressing variable numbers of EGF receptors (Table 2). The titers of viruses carrying EMO envelopes were reduced up to 1000-fold by EGF.R expression and there was a correlation between the density of EGF receptor expression and the magnitude of reduction in virus titre (Table 2B). When NR6-hEGF.R cells were pre-treated with rEGF, which down-regulates EGF.R as confirmed by antibody staining (not shown), titers of viruses coated with EGF-fusion envelopes were greatly enhanced, reaching the range of titres obtained on parental NR6 cells (Table 2A). These data confirm that interaction of virions with EGF receptors leads to their sequestration into an abortive entry pathway that does not lead to membrane fusion or cytoplasmic release of the viral cores.

Host Range and Competitive Sequestration of Viruses Carrying EA Envelopes

Table 1A shows that viruses incorporating EA envelopes can infect NIH3T3 mouse fibroblasts through the amphotropic MLV receptor. When titrated on a panel of human cell lines expressing varying densities of EGF receptors, the EA virus showed a selective inability to infect all of the EGF receptor-positive human cells in the panel (Table 1B). However, they could easily infect human B and T cell lines (K422 and Jurkat) which are devoid of EGF.R and are presumably infected through the amphotropic receptor (Table 1). These data suggested that the EA viruses were efficiently sequestered by EGF.R expressed on human cells and to confirm their competitive sequestration, they were tested on parental and EGF receptor-expressing NR6 mouse fibroblasts (Table 2A). EGF receptor expression on NR6 cells led to a competitive inhibition (100-fold) of viral infection which was reversible when the NR6 transfectants were pre-treated with EGF to block/downregulate their EGF receptors.

Some Sequestered Virus can be Rescued into an Infectious Entry Pathway.

After binding to receptor, EGF induces receptor dimerisation and its signal transduction, followed by ligand-receptor internalisation and routing to lysosomes, where EGF/EGF receptor complexes are degraded (Carpenter & Cohen, 1990 J. Biol. Chem 265 p7709–7712). The inventors suspected that viruses bound to EGF receptors might therefore be rapidly internalised into the cell and routed to lysosomes for degradation. When EMO-carrying viral particles were used to infect A431 cells treated with the inhibitor of lysosomal degradation, chloroquine, a significant increase of infectivity (by approximately 2 logs) was obtained (Table 3). This effect was specific to EGF.receptors as EGF.receptor negative cells, such as K422 cells, did not respond similarly (Table 3).

Materials and Methods

Cell Lines

TELCeB6 cell line was derived from the TELac2 line (Takeuchi et al, 1994 J. Virol. 68 p8001–8007) after transfection and clonal selection of cells containing a plasmid expressing MoMLV (Moloney murine leukemia virus) gag and pol proteins. TELCeB6 cells produce noninfectious viral core particles, carrying the MGFnlsLacZ reporter retroviral vector (Ferry et al, 1991 Proc. Natl. Acad. Sci. USA 88 p8377–8381). A431, TE671 (ATCC CRL8805), HT1080 (ATCC CCL121), EJ (Bubenik et al, 1973 Int. J. Cancer 11 p765–773) and EJ.Al, (an EJ clone that expresses ecotropic MLV receptors, Albritton et al, 1989 Cell 57 p659–666) were grown in DMEM (Gibco-BRL) supplemented with 10% fetal bovine serum (Gibco-BRL). K422 cells (Dyer et al, 1990 Blood 75 p709–714) and Jurkat T cells were grown in RPMI 1640 (GibcoBRL) supplemented with 10% fetal bovine serum (Gibco-BRL). NR6 murine fibroblasts lacking detectable EGF receptors (Schneider et al, 1986 Proc. Natl. Acad. Sci. USA 83 p333–336) and NR6-EGF.R (an NR6 subclone obtained after transfection of a plasmid expressing the human epidermal growth factor receptor) cells were kindly provided by G. Gill (La Jolla, USA). psi2 cells (Mann et al, 1983 Cell 33 p153–159) and GP+EAM12 cells (Markowitz et al, 1988 Virol. 167 p400–406) were derived from NIH-3T3 cells and express respectively MoMLV (ecotropic) and MLV-amphotropic envelopes which block the corresponding receptors (EcoR-1 and RAM-1) by interference. NIH3T3 clones transfected with EGF receptor expression constructs and expressing moderate or high levels of EGF receptors were kindly provided by Prof Thierry Velu (Erasmus Hospital, Brussels). NIH-3T3 and NIH-3T3-derived cell lines were grown in DMEM (Gibco-BRL) supplemented with 10% new born bovine serum (Gibco-BRL).

Chimeric Envelopes

A PCR-derived DNA fragment encoding the 53 aa of hEGF (Bell et al, 1986 Nucleic Acids Res. 14 p8427–8446) was generated using a cDNA template (ATCC 59957) and two primers:

OUEGF 5'- ATGCTCAGAGGGGTCAGTACGGCCCAGCCG GCCATGGCCAATAGTGACTCTGAATGTCCC - 3'

(Seq. ID No. 1) with an SfiI restriction site, and

OLEGF 5'- ACCTGAAGTGGTGGGAACTGCGCGC GGCCGCATGTGGGGGTCCAGACTCC - 3'

(Seq. ID No. 2) with a NotI site, and cloned after digestion with SfiI and NotI in either MoMLV SU for the EMO chimeric envelope or 4070A SU for the EA envelope (FIG. 1).

All envelope constructs were expressed as BglII-ClaI fragments (corresponding to positions 5408 and 7676 in MoMLV), cloned between BamHI and ClaI sites of the FBMosALF expression vector (Cosset et al, submitted), in which a phleo selectable marker (Gatignol et al, 1988 FEBS Lett 230 p171–175) fused to the PGK (phospho-glycerate kinase) gene poly-adenylation sequence was introduced downstream to the C57 MLV LTR of FB3 (Battini et al, 1992 J. Virol. 66 p1468–1475).

Production of Viruses

Envelope expression plasmids were transfected by calcium phosphate precipitation into TELCeB6 cells. Transfected cells were selected with phleomycin (50 mg/ml) and pools of phleomycin-resistant clones were used to harvest viruses from confluent cells after overnight incubation in DMEM and FBS (10%). These supernatants were used for ultracentrifugation to provide Western blot samples, for binding assays and for infection assays. Viruses (in 100 ml of producer cell supernatant) were also purified by gel-filtration on 2 ml columns (Bio-Rad) on a bed of S-1000 Sephacryl (Pharmacia). Fractions were obtained by elution with PBS at 4° C.

Immunoblots

Virus producer cells were lysed in a 20 mM Tris-HCl buffer (pH 7.5) containing 1% Triton-X100, 0.05% SDS, 5 mg/ml sodium deoxycholate, 150 mM NaCl, and 1 mM PMSF. Lysates were incubated for 10 min at 4° C. and were centrifuged for 10 min at 10,000×g to pellet the nuclei. Supernatants were then frozen at −70° C. until further analysis. Virus samples were obtained by ultracentrifugation of viral supernatants (10 ml) in a SW41 Beckman Rotor (30,000 RPM, 1 hr, 4° C.). Pellets were suspended in 100 μl of PBS (phosphate buffered saline), and frozen at −70° C. Samples (30 mg for cell lysates, or 10 μl for purified viruses) were mixed in a 375 mM Tris-HCl (pH 6.8) buffer containing 6% SDS, 30% b-mercapto-ethanol, 10% glycerol, and 0.06% bromophenol blue, boiled for 3 min, then run on 10% SDS acrylamide gels. After protein transfer onto nitrocellulose filters, immunostaining was performed in TBS (Tris base saline, pH 7.4) with 5% milk powder and 0.1% TWEEN. Antibodies (Quality Biotech Inc, USA) were goat antisera raised against either RLV (Rausher leukemia virus) gp70-SU protein or RLV p30-CA protein, and were diluted 1/1,000 and 1/10,000, respectively. Blots were developed using horseradish peroxidase (HRPO)-conjugated rabbit anti-goat antibodies (DAKO, UK) and an electrochemiluminescence kit (Amersham Life Science).

Binding Assays

Target cells were washed in PBS and detached by a 10 min incubation at 37° C. with versene 0.02% in PBS. Cells were washed in PBA (PBS with 2% FCS and 0.1% sodium azide). $10^6$ cells were incubated with viruses for 30 min at 4° C. Cells were then washed with PBA and incubated in PBA containing 1/200 of RLV gp70 immune serum for 30 min at 4° C. Cells were washed twice with PBA and incubated with rabbit anti-goat FITC-conjugated antibodies (DAKO, U.K.). 5 min before the two final washes in PBA, cells were stained with 20 mg/ml propidium iodide. Fluorescence of living cells was analysed with a fluorescent-activated cell sorter (FACSCan, Beckton Dickinson). For hEGF.R staining, 106 cells in 100 ml of PBA were incubated with 10 ml of anti-EGF.R antibodies (M886, DAKO, U.K.) for 30 min at 4° C.

Infection Assays

Target cells were seeded in 24 multi-well plates at a density of $3 \times 10^4$ cells per well or in 6-multi-well plates at a density of $2 \times 10$ cells per well. Viral supernatant dilutions containing 4 mg/ml polybrene were added and cells were incubated for 3–5 hrs at 37° C. Viral supernatant was then removed and cells were incubated in regular medium for 24–48 hrs. X-Gal staining was performed as previously described (Takeuchi et al, 1994 J. Virol. 68 p8001–8007).

To block EGF.R, target cells were incubated 30 min at 37° C. in a medium containing $10^{-6}$ M rEGF (236-EG, R&D Systems, U.K.). Cells were then washed and infections were carried out as previously described. To block lysosomal acidification, 100 mM chloroquine phosphate (Sigma, U.K.) was added to the medium for 6 hr from the start of the infection protocol after which the cells were washed and incubated in regular medium.

TABLE 1

Infection by virions expressing targeting envelopes

A. On mouse fibroblasts[b]

| env[a] | 3T3 | 3T3/E | 3T3/A |
|---|---|---|---|
| A | $10^7$ | $10^7$ | $10^2$ |
| MO | $10^7$ | <1 | $10^7$ |
| EMO | $10^5$ | <1 | $10^5$ |
| EA | $10^6$ | nd | $10^1$ |

B. On human cell lines[b]

| env[a] | A431 | HT108 | TE671 | K422 | Jurkat | EJE | J.A1 |
|---|---|---|---|---|---|---|---|
| EGFR | ++++ | ++ | + | − | − | ++ | ++ |
| A | $10^7$ | $10^7$ | $10^7$ | $10^5$ | $10^4$ | $10^6$ | $10^6$ |
| MO | <1 | <1 | <1 | <1 | <1 | <1 | $10^6$ |
| EMO | <1 | <1 | <1 | <1 | <1 | <1 | <1 |
| EA | <1 | <1 | $10^1$ | $10^4$ | $10^3$ | <1 | <1 | a: envelope expressed on lacZ virions
b: titres as lacZ-EFU/ml. Abbreviations for cell lines: 3T3: NIH3T3; 3T3/E: psi2; 3T3/A: GP + EAM12

TABLE 2

Inhibition of infection by EGF.R

A. NR6 cells[b]

| | NR6. | NR6-wt hEGF.R. | |
|---|---|---|---|
| env[a] | titre | −rEGF[c] titre | +rEGF titre |
| MO | $1 \times 10^5$ | $5 \times 10^5$ | $5 \times 10^5$ |
| EMO | $5 \times 10^4$ | $1 \times 10^3$ | $10^5$ |
| A | $7 \times 10^4$ | $2 \times 10^5$ | $2 \times 10^5$ |

TABLE 2-continued

Inhibition of infection by EGF.R

| EA | $2 \times 10^5$ | $3 \times 10^3$ | $5 \times 10^5$ |
|---|---|---|---|

B. NIH3T3 cells[b]

| EGFR No. env[a] | 10,000 titre | 80,000 titre | 400,000 titre |
|---|---|---|---|
| MO | $10^6$ | $10^6$ | $10^6$ |
| EMO | $10^5$ | $10^4$ | $10^3$ |

[a]envelope expressed on lacZ virions
[b]titres as lacZ-EFU/ml.
[c]cells were (+) or were not (−) pre-incubated with $10^{-6}$ M recombinant EGF for 30 min at 37° C.

TABLE 3

Effect of chloroquine on infection

| | NIH3T3[b]. | | A431[b]. | | TE671[b]. | | K422[b]. | |
|---|---|---|---|---|---|---|---|---|
| env[a] | − | + | − | + | − | + | − | + |
| MO | $10^6$ | $5 \times 10^5$ | <1 | 6 | < | 1 | <1 | <1 |
| EMO | $10^5$ | $5 \times 10^4$ | 1 | 225 | <1 | 46 | <1 | <1 |

[a]envelope expressed on lacZ virions
[b]titres as lacZ EFU/ml. Cells were treated (+) or not (−) with chloroquine.

Example 2

The investigators and their colleagues wished to determine whether they could selectively impair the efficiency of gene delivery by viruses incorporating chimaeric 4070A envelope proteins displaying a ligand other than EGF. To this end they cloned the coding sequence of human insulin-like growth factor-1 (IGF-1) (Hodgson et al., 1995 Eur. J. Biochem. 233, 299–309), in frame, into a SfiI-NotI cloning site which had been introduced 5' of the first codon of the 4070A MLV env gene (Nilson et al., 1996 Gene Therapy 3, 280–286), producing construct IA. In addition, the IGF-I coding sequence was cloned, in frame, into a SfiI-NotI site 5' of the sequence coding for a Factor Xa protease cleavage site (amino acid residues IEGR), which had been previously introduced 5' of the first codon of the env gene of 4070A MLV (Nilson et al., 1996 cited above). This construct was designated IXA.

The chimaeric envelope constructs were then transfected into the complementing cell line TelCeB6. Western blot analysis of pelleted viruses revealed that both IA and IXA envelope proteins were efficiently incorporated into viral particles. The efficiency of β-galactosidase gene transfer to mouse NIH 3T3 cells by viral particles bearing IA and IXA envelope proteins was comparable to that of particles incorporating wild-type 4070A envelope proteins, (NIH-3T3 cells being IGF-1 receptor negative).

However, viral particles incorporating chimaeric IA and IXA envelope proteins did not efficiently transfer the β-galactosidase gene to type-I IGF-receptor positive human MCF-7 cells or mouse 3T3 cells which had been transfected with type-I IGFR (Insulin-like growth factor-1 receptor) (Lammers et al., 1989 EMBO J. 8, 1369–1375). The titres produced by infection of the IGFR-positive cell lines with the IA and IXA viral particles were up to 1000-fold reduced relative to the titres produced by control viruses incorporating unmodified 4070A envelope proteins. Factor Xa protease cleavage of viral particles incorporating IXA envelope proteins restored the titre produced on MCF-7 and IGFR/3T3 cells to wild-type levels. This demonstrated that the titre reductions for IA and IXA viruses on type-I IGFR-positive cell lines had been due to the displayed IGF-I domain.

In an attempt to prove that the aforementioned reduction in titre was due to specific binding of the displayed IGF-I to the type-I IGFR, the inventors and their colleagues determined the efficiency of β-galactosidase gene transfer to IGFR/3T3 cells by IA-incorporating viral particles in the presence of increasing concentrations of insulin. Insulin has about a 100-fold reduced affinity for the Type-I IGF-receptor relative to IGF-I (Steele-Perkins et al., 1988 J. Biol. Chem. 263, 11486–11492). The Kd of insulin for the type-I IGF receptor has been reported to be around 300 nm (Hodgson et al., 1995 cited above), which corresponds to a 50% displacement of IGF-I at approximately 1.5 μg/ml insulin. A maximal increase in titre of about 100-fold was obtained in the presence of 100 μg/ml insulin. A modest increase in titre of about three-fold was observed in the presence of as little as 1 μg/ml insulin. This demonstrates that the proposed assay can be used to detect ligands with at least a 100-fold reduced affinity for the type-I IGF receptor.

The infection assays in which insulin was present were performed essentially as described above except that insulin was added at the indicated concentrations 10 minutes prior to addition of the viral supernatant to cells.

TABLE 4

A. On mouse NIH 3T3 fibroblasts

| env | −Xa | +Xa |
|---|---|---|
| A | $\sim 10^6$ | $\sim 10^6$ |
| IA | $\sim 10^6$ | $\sim 10^6$ |
| IXA | $\sim 10^6$ | $\sim 10^6$ |

B. On IGFR-positive cell-lines

| | MCF-7 | | 1GFR/3T3 | |
|---|---|---|---|---|
| env | −Xa | +Xa | −Xa | +Xa |
| A | $\sim 10^6$ | $\sim 10^6$ | $\sim 10^6$ | $\sim 10^6$ |
| IA | $6.4 \times 10^2$ | $4.8 \times 10^3$ | $5.1 \times 10^2$ | $1.6 \times 10^3$ |
| IXA | $9.2 \times 10^2$ | $\sim 10^6$ | $5.6 \times 10^2$ | $\sim 10^6$ |

TABLE 5 inhibition of IGFR/3T3 infection by insulin

| | Insulin concentration | | | |
|---|---|---|---|---|
| env | 0 | 1 μg/ml | 10 μg/ml | 100 μg/ml |
| A | $\sim 10^6$ | n.d. | n.d. | $\sim 10^6$ |
| IA | $1.5 \times 10^3$ | $4.4 \times 10^3$ | $1.6 \times 10^4$ | $\sim 10^5$ |

Assay for Altered Receptor Density

The assay format described in this invention can be employed for the detection of substances which influence receptor density. Receptor density is modulated by factors which influence the level of receptor gene expression and receptor biosynthesis or by factors which enhance the rate of receptor endocytosis and degradation. For example, growth factor treatment of cells causes rapid capping and endocytosis of receptor-ligand complexes resulting in a substantial decrease in the number of surface receptors for the growth factor in question (A Sorkin and C M Walters, 1993, Bioessays, 15, p375–382). In the majority of cell types studied, EGF receptor downregulation occurs rapidly after exposure to EGF, leading to internalisation of greater than 80% of surface receptors within 2 hours (Carpenter and Cohen, 1976, J Cell Biol, 71, p159; Beguinot et al., 1984, PNAS, 81, p2384; Dunn and Hubbard, 1984, J Cell Biol, 98, p2148; Gilligan et al., 1992, Exp Cell Res, 200, p235).

β-galactosidase-transducing retroviral vectors displaying EA1 chimaeric envelopes (comprising an EGFR-binding polypeptide fused to the N-terminus of the 4070A MLV envelope glycoprotein) are known to be capable of binding either to the 4070A envelope glyoprotein) are known to be capable of binding either to the 4070A envelope glycoprotein receptor, RAM-1, leading to transfer and expression of the β-galactosidase gene, or to EGFR leading to inhibition of β-galactosidase gene transfer and expression (Nilson BHK et al., 1996, Gene Therapy, 3, p280–286). It was shown in the same study that the infectivity of these vectors is strongly inhibited on human EGFR-positive cells (El, HT1080 and A431) and that infectivity, at least on EJ cells, can be restored by adding 1 μM EGF to the culture medium at the time of infection (i.e. during exposure to the vector particles).

Example 3

Assay for a Substance Causing a Reduction in the Cell Surface Density of EGF Receptors EGFR-expressing human cell lines [EJ bladder carcinoma cells and HT1080 fibrosarcoma cells (Nilson BHK et al., 1996, Gene Therapy, 3, p280), and PLC/PRF/5 hepatoma cells (Gilligan et al., 1992, Exp Cell Res, 200, p235)] are seeded at $2 \times 10^5$ cells/well in six-well plates and incubated at 37° C. overnight in regular medium. For varying periods of time (ten minutes up to four hours) before they are due to be infected, the target cells are exposed to varying concentrations (1 nM up to 1 μM) of EGF or to other test substances. Control target cells are maintained in regular medium. Immediately prior to infection, the target cells are washed three times with DMEM. Infections are performed using 0.45 μM-filtered, serum-free producer cell supernatants containing β-galactosidase-transducing retroviruses incorporating EA1 chimaeric envelopes (Nilson BHK et al., 1996, Gene Therapy, 3, 280–286). Target cells are incubated for 2 hours with 1 ml of EA1 viral supernatant diluted in 2.5 ml serum-free medium containing 8 μg/ml polybrene. The retroviral supernatant is then removed and the cells are incubated with regular medium for 48–72 hours. X-Gal staining for detection of β-galactosidase activity is then performed and viral titre (enzyme forming units/ml) is calculated by counting blue stained colonies microscopically with the use of a grid placed underneath the 6 well plates.

Viral titres are low on the control target cells. Higher viral titres are obtained on target cells that have been exposed to EGF prior to infection because their surface density of EGFR is reduced. The enhancement of titre is greater at higher concentrations of EGF and with longer durations of exposure. Higher viral titres are also obtained on target cells that have been exposed to test substances which downmodulate EGF receptors.

What is claimed is:

1. A method of testing a substance for the ability to interfere with or increase transfer of a label between a lipid enveloped viral particle and a cell, wherein a first member of a specific binding pair is present on the surface of a lipid enveloped particle comprising a transferrable label, said first member of the binding pair being characterized in that it can bind to a second member of the specific binding pair present on the surface of a cell, the lipid envelope of the particle being capable of fusing with the membrane of the cell so as to transfer the label to the cell, said transfer being inhibited by formation or oligomerization of a complex between the first and second members of the binding pair, wherein the method comprises reacting the particle and the cell in the presence of the substance under test, and detecting the amount of label transferred, wherein the amount of label transferred is compared to a standard amount of transferred label detected in a reaction wherein the particle and cell are contacted under conditions which allow for binding of the first and second members of the specific binding pair in the absence of the substance under test, wherein an increase in the amount of label transfered in the presence of the substance under test relative to the standard is indicative of interference with formation or oligomerization of a complex.

2. The method of claim 1, wherein the lipid enveloped particle is a synthetic lipid vesicle or a liposome.

3. The method of claim 1, wherein the lipid enveloped particle is a lipid enveloped virus.

4. The method of claim 3, wherein the particle is a retrovirus.

5. The method of claim 1, wherein the particle comprises a polypeptide capable of enhancing fusion between the particle and the cell.

6. The method of claim 5, wherein the polypeptide is glycosylated.

7. The method of claim 5, wherein the polypeptide is of viral origin.

8. The method of claim 5, wherein the polypeptide comprises an effective portion of a retroviral envelope glycoprotein or influenza virus haemagglutinin.

9. The method of claim 5, wherein the polypeptide comprises a substantially intact viral envelope glycoprotein.

10. The method of claim 5, wherein the cell expresses a surface receptor for the polypeptide.

11. The method of claim 1, wherein the cell is eukaryotic.

12. The method of claim 1, wherein the cell is mammalian.

13. The method of claim 1, wherein the transferrable label is radioactive, fluorescent, a reporter gene, or an enzyme.

14. The method of claim 13, wherein the reporter gene codes for the expression of βgalactosidase.

15. The method of claim 1, wherein the first member of the specific binding pair is present on the surface of the particle as a fusion polypeptide.

16. The method of claim 15, wherein the first member of the specific binding pair is expressed as a fusion with a polypeptide capable of enhancing fusion between the particle and the cell.

17. The method according to claim 16, wherein the first member of the specific binding pair is expressed as an N-terminal fusion with an effective portion of a C type retroviral envelope glycoprotein.

18. The method of claim 16, wherein the first member of the specific binding pair is expressed as an N-terminal fusion with an effective portion of 4070A MLV envelope glycoprotein.

19. The method of claim 1, wherein the amount of said label transferred is reduced in the presence of said substance under test and the amount of said second member of the specific binding pair present on the surface of said cell is reduced.

20. The method of claim 1 wherein the amount of said label transferred is reduced in the presence of said substance under test as a result of inhibition of oligomerization of said complex of first and second members of a specific binding pair.

21. A kit comprising:
a lipid enveloped particle comprising a first member of a specific binding pair and a transferrable label;
a cell displaying a second member of the specific binding pair, the lipid envelope of the particle being capable of fusing with the membrane of the cell so as to transfer the label to the cell, said transfer being inhibited by formation or oligomerization of a complex between the first and second members of the specific binding pair;

a control substance that binds to the second member of the specific binding pair so as to prevent formation of a complex between the first and second members of the specific binding pair; and packaging materials therefor.

22. The composition kit of claim 21, further comprising a substance under test for its ability to affect the binding of the first and second members of the specific binding pair.

* * * * *

SEQUENCE LISTING (1) GENERAL INFORMATION:

(iii) NUMBER OF SEQUENCES:2

(2) INFORMATION FOR SEQ ID NO: 1:

(i) SEQUENCE CHARACTERISTICS:
       (A) LENGTH: 60 base pairs
       (B) TYPE: nucleic acid
       (C) STRANDEDNESS: single
       (D) TOPOLOGY: linear (xi) SEQUENCE DESCRIPTION: SEQ ID NO: 1:

ATGCTCAGAG GGGTCAGTAC GGCCCAGCCG GCCATGGCCA ATAGTGACTC TGAATGTCCC        60

(2) INFORMATION FOR SEQ ID NO: 2:

(i) SEQUENCE CHARACTERISTICS:
       (A) LENGTH: 50 base pairs
       (B) TYPE: nucleic acid
       (C) STRANDEDNESS: single
       (D) TOPOLOGY: linear (xi) SEQUENCE DESCRIPTION: SEQ ID NO: 2:

ACCTGAAGTG GTGGGAACTG CGCGCGGCCG CATGTGGGGG TCCAGACTCC        50